United States Patent
Noda et al.

(10) Patent No.: US 10,851,141 B2
(45) Date of Patent: Dec. 1, 2020

(54) MUTANT BEETLE LUCIFERASE, GENE, RECOMBINANT VECTOR, TRANSFORMANT, AND METHOD FOR PREPARING MUTANT BEETLE LUCIFERASE

(71) Applicant: DKK-TOA Corporation, Tokyo (JP)

(72) Inventors: Kenichi Noda, Tokyo (JP); Satoshi Yawata, Tokyo (JP); Ai Shimomura, Tokyo (JP)

(73) Assignee: DKK-TOA Corporation, Tokyo (JP)

( * ) Notice: Subject to any disclaimer, the term of this patent is extended or adjusted under 35 U.S.C. 154(b) by 0 days.

(21) Appl. No.: 16/311,301

(22) PCT Filed: Jun. 19, 2017

(86) PCT No.: PCT/JP2017/022486
§ 371 (c)(1),
(2) Date: Dec. 19, 2018

(87) PCT Pub. No.: WO2017/221873
PCT Pub. Date: Dec. 28, 2017

(65) Prior Publication Data
US 2019/0352350 A1 Nov. 21, 2019

(30) Foreign Application Priority Data

Jun. 21, 2016 (JP) ................... 2016-122545

(51) Int. Cl.
*C12N 15/10* (2006.01)
*C12N 15/09* (2006.01)
*C12P 21/02* (2006.01)
*C07H 21/04* (2006.01)
*C07K 14/435* (2006.01)
*C12N 9/02* (2006.01)
*C12N 15/63* (2006.01)

(52) U.S. Cl.
CPC ...... *C07K 14/43563* (2013.01); *C12N 9/0069* (2013.01); *C12N 15/63* (2013.01); *C12P 21/02* (2013.01); *C12Y 113/12007* (2013.01)

(58) Field of Classification Search
CPC ........ C12N 9/0069; C12P 21/02; C07H 21/04
See application file for complete search history.

(56) References Cited

U.S. PATENT DOCUMENTS

| 6,387,675 | B1 | 5/2002 | Wood et al. | |
|---|---|---|---|---|
| 6,602,677 | B1 * | 8/2003 | Wood ................... | C12N 9/0069 435/189 |
| 8,003,350 | B2 * | 8/2011 | Fujii ............. | C12Y 113/12007 435/69.5 |
| 2009/0305353 | A1 | 12/2009 | Fujii et al. | |

FOREIGN PATENT DOCUMENTS

| CN | 103483229 A | 1/2014 |
|---|---|---|
| JP | 2666561 B | 10/1997 |
| JP | 11239493 A | 9/1999 |
| JP | 3048466 B | 6/2000 |
| JP | 2000197484 A | 7/2000 |
| JP | 2001518799 A | 10/2001 |
| JP | 2007097577 A | 4/2007 |
| JP | 2008289475 A | 12/2008 |
| JP | 2011083289 A | 4/2011 |
| JP | 2014062785 A | 4/2014 |
| WO | 2004059294 A2 | 7/2004 |
| WO | 2016079310 A1 | 5/2016 |

OTHER PUBLICATIONS

Fujii, H. et al., Increase in bioluminescence intensity of firefly luciferase using genetic modification, Analytical Biochemistry, 2007, vol. 366, pp. 131-136, ISSN: 0003-2697.
Modestova, Y. et al., Biochimica et Biophysica Acta, Proteins and Proteomics, 2014, vol. 1844, No. 9, pp. 1463-1471.
PCT Office, International Search Report issued in corresponding PCT/JP2017/022486 dated Sep. 5, 2017, 4 pages.
Japanese Patent Office, Office Action issued in corresponding JP 2016-122545 dated Oct. 23, 2018, 10 pages.
European Patent Office, Search Report issued in EP 17815341.7 dated Dec. 5, 2019, 12 pages.

* cited by examiner

*Primary Examiner* — Maryam Monshipouri
(74) *Attorney, Agent, or Firm* — Wood Herron & Evans LLP

(57) ABSTRACT

The present invention provides a mutant beetle luciferase and the like, having mutation in which the amino acid corresponding to valine at position 288 in the amino acid sequence of wild-type *Photinus pyralis* luciferase is isoleucine, leucine or phenylalanine, mutation in which the amino acid corresponding to leucine at position 376 in the aforementioned sequence is proline, mutation in which the amino acid corresponding to glutamic acid at position 455 in the aforementioned sequence is valine, alanine, serine, leucine, isoleucine or phenylalanine, or mutation in which the amino acid corresponding to glutamic acid at position 488 in the aforementioned sequence is valine, alanine, serine, leucine, isoleucine or phenylalanine, in the amino acid sequence encoding a wild-type beetle luciferase, and characterized in that a luminescence intensity due to a luciferin-luciferase luminescence reaction in a 0.9% by mass NaCl solution is 50% or more of that in a NaCl-free solution.

6 Claims, 2 Drawing Sheets
Specification includes a Sequence Listing.

SEQUENCE LISTING

```
<160> NUMBER OF SEQ ID NOS: 15

<210> SEQ ID NO 1
<211> LENGTH: 550
<212> TYPE: PRT
<213> ORGANISM: Photinus pyralis

<400> SEQUENCE: 1

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95
```

```
Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
```

-continued

```
                515                 520                 525
Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 2
<211> LENGTH: 548
<212> TYPE: PRT
<213> ORGANISM: Luciola lateralis

<400> SEQUENCE: 2

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Pro
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335
```

-continued

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
            355                 360                 365

Pro Leu Phe Lys Ala Lys Val Ile Asp Leu Asp Thr Lys Lys Thr Leu
        370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 3
<211> LENGTH: 548
<212> TYPE: PRT
<213> ORGANISM: Luciola cruciata

<400> SEQUENCE: 3

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

```
Arg Gly Tyr Gln Cys Leu Asp Thr Phe Ile Lys Arg Asn Thr Pro Pro
            165                 170                 175

Gly Phe Gln Ala Ser Ser Phe Lys Thr Val Glu Val Asp Arg Lys Glu
        180                 185                 190

Gln Val Ala Leu Ile Met Asn Ser Ser Gly Thr Gly Leu Pro Lys
        195                 200                 205

Gly Val Gln Leu Thr His Glu Asn Thr Val Thr Arg Phe Ser His Ala
        210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Leu Gly
            245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
        290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
            355                 360                 365

Pro Leu Phe Lys Ala Lys Val Ile Asp Leu Asp Thr Lys Lys Ser Leu
        370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
        450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Arg Ala Ile Arg Glu Ile Leu Lys Lys Pro
        530                 535                 540

Val Ala Lys Met
545

<210> SEQ ID NO 4
<211> LENGTH: 543
```

<212> TYPE: PRT
<213> ORGANISM: Pyrophorus plagiophthalamus

<400> SEQUENCE: 4

```
Met Met Lys Arg Glu Lys Asn Val Val Tyr Gly Pro Glu Pro Lys His
1               5                   10                  15

Pro Leu Gly Asn Phe Thr Ala Gly Glu Met Leu Tyr Asn Ala Leu His
            20                  25                  30

Lys His Ser His Ile Pro Gln Ala Ile Leu Asp Val Met Gly Asn Glu
        35                  40                  45

Ser Leu Ser Tyr Gln Glu Phe Phe Asp Thr Thr Val Lys Leu Gly Gln
    50                  55                  60

Ser Leu Gln Asn Cys Gly Tyr Lys Met Asn Asp Val Val Ser Ile Cys
65                  70                  75                  80

Ala Glu Asn Asn Lys Arg Phe Phe Ile Pro Ile Ile Ser Ala Trp Tyr
                85                  90                  95

Ile Gly Met Val Val Ala Pro Val Asn Glu Asp Tyr Ile Pro Asp Glu
            100                 105                 110

Leu Cys Lys Val Thr Gly Ile Ser Lys Pro Ile Leu Val Phe Thr Thr
        115                 120                 125

Arg Lys Ile Leu Pro Lys Val Leu Glu Val Lys Asp Arg Thr Asn Tyr
    130                 135                 140

Ile Lys Arg Ile Ile Ile Leu Asp Ser Glu Glu Asn Leu Leu Gly Cys
145                 150                 155                 160

Glu Ser Leu His Asn Phe Met Ser Arg Tyr Ser Asp Asn Asn Leu Gln
                165                 170                 175

Thr Phe Lys Pro Leu His Tyr Asp Pro Val Asp Gln Val Ala Ala Ile
            180                 185                 190

Leu Cys Ser Ser Gly Thr Thr Gly Leu Pro Lys Gly Val Met Gln Thr
        195                 200                 205

His Arg Asn Ile Cys Val Arg Leu Thr His Ala Ser Asp Pro Arg Val
    210                 215                 220

Gly Thr Gln Leu Ile Pro Gly Val Ser Val Leu Ala Tyr Leu Pro Phe
225                 230                 235                 240

Phe His Ala Phe Gly Phe Ser Ile Asn Leu Gly Tyr Phe Met Val Gly
                245                 250                 255

Leu Arg Val Val Met Leu Arg Arg Phe Asn Gln Glu Val Phe Leu Lys
            260                 265                 270

Ala Ile Gln Asp Tyr Glu Val Arg Ser Val Ile Asn Val Pro Ser Thr
        275                 280                 285

Ile Leu Phe Leu Ser Lys Ser Pro Leu Val Asp Lys Tyr Asp Leu Ser
    290                 295                 300

Thr Leu Ala Glu Leu Cys Cys Gly Ala Ala Pro Leu Ala Lys Glu Val
305                 310                 315                 320

Ala Glu Ile Ala Val Lys Arg Leu Asn Leu Pro Gly Ile Arg Cys Gly
                325                 330                 335

Tyr Gly Leu Thr Glu Ser Thr Ser Ala Asn Ile His Thr Leu His Asn
            340                 345                 350

Glu Phe Lys Ser Gly Ser Leu Gly Lys Val Thr Pro Tyr Met Ala Ala
        355                 360                 365

Lys Ile Ile Asp Arg Asn Thr Gly Glu Ala Leu Gly Pro Asn Gln Val
    370                 375                 380

Gly Glu Leu Cys Ile Trp Gly Pro Met Val Thr Lys Gly Tyr Val Asn
385                 390                 395                 400
```

```
Asn Pro Gln Ala Thr Lys Glu Ala Ile Asp Asp Gly Trp Leu His
                405                 410                 415
Ser Gly Asp Phe Gly Tyr Tyr Asp Glu Asp Glu Tyr Phe Tyr Ile Val
            420                 425                 430
Asp Arg Tyr Lys Glu Leu Ile Lys Tyr Lys Gly Tyr Gln Val Ala Pro
        435                 440                 445
Val Glu Leu Glu Glu Ile Leu Leu Gln His Pro Gly Ile Arg Asp Val
    450                 455                 460
Ala Val Val Gly Ile Pro Asp Ile Glu Ala Gly Leu Pro Ala Gly
465                 470                 475                 480
Phe Val Val Lys Gln Pro Gly Ala Gln Leu Thr Ala Lys Glu Val Tyr
                485                 490                 495
Asp Phe Leu Ala Gln Arg Val Ser His Ser Lys Tyr Leu Arg Gly Gly
            500                 505                 510
Val Arg Phe Val Asp Ser Ile Pro Arg Asn Val Thr Gly Lys Ile Ser
        515                 520                 525
Arg Lys Glu Leu Arg Glu Ala Leu Met Glu Lys Ala Ser Lys Leu
    530                 535                 540
```

<210> SEQ ID NO 5
<211> LENGTH: 1650
<212> TYPE: DNA
<213> ORGANISM: Photinus pyralis

<400> SEQUENCE: 5

| | | | | |
|---|---|---|---|---|
| atggaagacg | ccaaaaacat | aaagaaaggc | ccggcgccat | tctatcctct agaggatgga | 60 |
| accgctggag | agcaactgca | taaggctatg | aagagatacg | ccctggttcc cggaacaatt | 120 |
| gcttttacag | atgcacatat | cgaggtgaac | atcacgtacg | cggaatactt cgaaatgtcc | 180 |
| gttcggttgg | cagaagctat | gaaacgatat | gggctgaata | caaatcacag aatcgtcgta | 240 |
| tgcagtgaaa | actctcttca | attctttatg | ccggtgttgg | gcgcgttatt tatcggagtt | 300 |
| gcagttgcgc | ccgcgaacga | catttataat | gaacgtgaat | tgctcaacag tatgaacatt | 360 |
| tcgcagccta | ccgtagtgtt | tgtttccaaa | aaggggttgc | aaaaaatttt gaacgtgcaa | 420 |
| aaaaaattac | caataatcca | gaaaattatt | atcatggatt | ctaaaacgga ttaccaggga | 480 |
| tttcagtcga | tgtacacgtt | cgtcacatct | catctacctc | ccggttttaa tgaatacgat | 540 |
| tttgtaccag | agtcctttga | tcgtgacaaa | acaattgcac | tgataatgaa ttcctctgga | 600 |
| tctactgggt | tacctaaggg | tgtggcccct | ccgcatagaa | ctgcctgcgt cagattctcg | 660 |
| catgccagag | atcctatttt | tggcaatcaa | atcattccgg | atactgcgat tttaagtgtt | 720 |
| gttccattcc | atcacggttt | tggaatgttt | actacactcg | gatatttgat atgtggattt | 780 |
| cgagtcgtct | taatgtatag | atttgaagaa | gagctgtttt | tacgatccct tcaggattac | 840 |
| aaaattcaaa | gtgcgttgct | agtaccaacc | ctattttcat | tcttcgccaa aagcactctg | 900 |
| attgacaaat | acgatttatc | taatttacac | gaaattgctt | ctgggggcgc acctctttcg | 960 |
| aaagaagtcg | gggaagcggt | tgcaaaacgc | ttccatcttc | cagggatacg acaaggatat | 1020 |
| gggctcactg | agactacatc | agctattctg | attacacccg | aggggatga taaaccgggc | 1080 |
| gcggtcggta | aagttgttcc | attttttgaa | gcgaaggttg | tggatctgga taccgggaaa | 1140 |
| acgctgggcg | ttaatcagag | aggcgaatta | tgtgtcagag | gacctatgat tatgtccggt | 1200 |
| tatgtaaaca | atccggaagc | gaccaacgcc | ttgattgaca | aggatggatg ctacattct | 1260 |
| ggagacatag | cttactggga | cgaagacgaa | cacttcttca | tagttgaccg cttgaagtct | 1320 |

```
ttaattaaat acaaaggata tcaggtggcc cccgctgaat tggaatcgat attgttacaa    1380 cacccccaaca tcttcgacgc gggcgtggca ggtcttcccg acgatgacgc cggtgaactt    1440
cccgccgccg ttgttgtttt ggagcacgga agacgatga cggaaaaaga gatcgtggat     1500
tacgtcgcca gtcaagtaac aaccgcgaaa agttgcgcg gaggagttgt gtttgtggac     1560
gaagtaccga aaggtcttac cggaaaactc gacgcaagaa aaatcagaga gatcctcata    1620
aaggccaaga agggcggaaa gtccaaattg                                    1650
```

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6

```
gactccatgg aagacgccaa aaac                                            24
```

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7

```
gacactcgag caatttggac tttccgcc                                        28
```

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8

```
cacgatcatg agcacccgtg g                                               21
```

<210> SEQ ID NO 9
<211> LENGTH: 1656
<212> TYPE: DNA
<213> ORGANISM: Artificial Sequence
<220> FEATURE:
<223> OTHER INFORMATION: Nucleotide sequence encoding a mutant(V288I)

<400> SEQUENCE: 9

```
atggaagacg ccaaaaacat aaagaaaggc ccggcgccat tctatcctct agaggatgga    60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
```

| | |
|---|---|
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct aataccaacc ctattttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg aggggatga taaaccgggc | 1080 |
| gcggtcggta agttgttcc attttttgaa gcgaaggttg tggatctgga taccgggaaa | 1140 |
| acgctgggcg ttaatcagag aggcgaatta tgtgtcagag acctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga agacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aggtcttac cggaaaaactc gacgcaagaa aaatcagaga gatcctcata | 1620 |
| aaggccaaga agggcggaaa gtccaaattg ctcgag | 1656 |

<210> SEQ ID NO 10
<211> LENGTH: 1656
<212> TYPE: DNA
<213> ORGANISM: Artificial Sequence
<220> FEATURE:
<223> OTHER INFORMATION: Nucleotide sequence encoding a mutant(L376P)

<400> SEQUENCE: 10

| | |
|---|---|
| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aagggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct agtaccaacc ctattttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |

```
gggctcactg agactacatc agctattctg attacacccg aggggatga taaaccgggc      1080 gcggtcggta aagttgttcc attttttgaa gcgaaggttg tggatccgga taccgggaaa      1140
acgctgggcg ttaatcagag aggcgaatta tgtgtcagag gacctatgat tatgtccggt      1200
tatgtaaaca atccggaagc gaccaacgcc ttgattgaca aggatggatg gctacattct      1260
ggagacatag cttactggga cgaagacgaa cacttcttca tagttgaccg cttgaagtct      1320
ttaattaaat acaaaggata tcaggtggcc cccgctgaat tggaatcgat attgttacaa      1380 cacccccaaca tcttcgacgc gggcgtggca ggtcttcccg acgatgacgc cggtgaactt      1440
cccgccgccg ttgttgtttt ggagcacgga agacgatga cggaaaaaga gatcgtggat      1500
tacgtcgcca gtcaagtaac aaccgcgaaa aagttgcgcg gaggagttgt gtttgtggac      1560
gaagtaccga aagtcttac cggaaaaactc gacgcaagaa aaatcagaga gatcctcata      1620
aaggccaaga agggcggaaa gtccaaattg ctcgag                              1656

<210> SEQ ID NO 11
<211> LENGTH: 1656
<212> TYPE: DNA
<213> ORGANISM: Artificial Sequence
<220> FEATURE:
<223> OTHER INFORMATION: Nucleotide sequence encoding a mutant(E455V)

<400> SEQUENCE: 11
atggaagacg ccaaaaacat aaagaaaggc ccggcgccat tctatcctct agaggatgga        60
accgctggag agcaactgca taaggctatg aagagatacg ccctggttcc tggaacaatt       120
gcttttacag atgcacatat cgaggtgaac atcacgtacg cggaatactt cgaaatgtcc       180
gttcggttgg cagaagctat gaaacgatat gggctgaata caaatcacag aatcgtcgta       240
tgcagtgaaa actctcttca attctttatg ccggtgttgg gcgcgttatt tatcggagtt       300
gcagttgcgc ccgcgaacga catttataat gaacgtgaat tgctcaacag tatgaacatt       360
tcgcagccta ccgtagtgtt tgtttccaaa aaggggttgc aaaaaatttt gaacgtgcaa       420
aaaaaattac caataatcca gaaaattatt atcatggatt ctaaaacgga ttaccaggga       480
tttcagtcga tgtacacgtt cgtcacatct catctacctc ccggttttaa tgaatacgat       540
tttgtaccag agtcctttga tcgtgacaaa acaattgcac tgataatgaa ttcctctgga       600
tctactgggt tacctaaggg tgtggccctt ccgcatagaa ctgcctgcgt cagattctcg       660
catgccagag atcctatttt tggcaatcaa atcattccgg atactgcgat tttaagtgtt       720
gttccattcc atcacggttt tggaatgttt actacactcg atatttgat atgtggattt       780 cgagtcgtct taatgtatag atttgaagaa gagctgtttt tacgatccct tcaggattac       840
aaaattcaaa gtgcgttgct agtaccaacc tatttcat tcttcgccaa aagcactctg       900
attgacaaat acgatttatc taatttacac gaaattgctt ctggggcgc acctctttcg       960 aaagaagtcg ggaagcggt tgcaaaacgc ttccatcttc cagggatacg acaaggatat      1020
gggctcactg agactacatc agctattctg attacacccg aggggatga taaaccgggc      1080 gcggtcggta aagttgttcc attttttgaa gcgaaggttg tggatctgga taccgggaaa      1140
acgctgggcg ttaatcagag aggcgaatta tgtgtcagag gacctatgat tatgtccggt      1200
tatgtaaaca atccggaagc gaccaacgcc ttgattgaca aggatggatg gctacattct      1260
ggagacatag cttactggga cgaagacgaa cacttcttca tagttgaccg cttgaagtct      1320
ttaattaaat acaaaggata tcaggtggcc cccgctgaat tggtatcgat attgttacaa      1380
```

| cacccccaaca tcttcgacgc gggcgtggca ggtcttcccg acgatgacgc cggtgaactt | 1440 |
| cccgccgccg ttgttgtttt ggagcacgga aagacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aaggtcttac cggaaaaactc gacgcaagaa aaatcagaga gatcctcata | 1620 |
| aaggccaaga agggcggaaa gtccaaattg ctcgag | 1656 |

<210> SEQ ID NO 12
<211> LENGTH: 1656
<212> TYPE: DNA
<213> ORGANISM: Artificial Sequence
<220> FEATURE:
<223> OTHER INFORMATION: Nucleotide sequence encoding a mutant(E488V)

<400> SEQUENCE: 12

| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggcccct tccgcataga actgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct agtaccaacc ctattttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc attttttgaa gcgaaggttg tggatctgga taccgggaaa | 1140 |
| acgctgggcg ttaatcagag aggcgaatta tgtgtcagag acctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| cacccccaaca tcttcgacgc gggcgtggca ggtcttcccg acgatgacgc cggtgaactt | 1440 |
| cccgccgccg ttgttgtttt ggtgcacgga aagacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aaggtcttac cggaaaaactc gacgcaagaa aaatcagaga gatcctcata | 1620 |
| aaggccaaga agggcggaaa gtccaaattg ctcgag | 1656 |

<210> SEQ ID NO 13
<211> LENGTH: 1656

<212> TYPE: DNA
<213> ORGANISM: Artificial Sequence
<220> FEATURE:
<223> OTHER INFORMATION: Nucleotide sequence encoding a
      mutant(V288I+L376P)

<400> SEQUENCE: 13

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aagggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct tccgcataga ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780
cgagtcgtct taatgtatag atttgaagaa gagctgtttt tacgatccct tcaggattac     840
aaaattcaaa gtgcgttgct aataccaacc ctatttcat tcttcgccaa aagcactctg     900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacacccg agggggatga taaaccgggc    1080
gcggtcggta agttgttcc atttttttgaa gcgaaggttg tggatccgga taccgggaaa    1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
cacccccaaca tcttcgacgc gggcgtggca ggtcttcccg acgatgacgc cggtgaactt    1440
cccgccgccg ttgttgtttt ggagcacgga aagacgatga cggaaaaaga tcgtggat      1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg ctcgag                              1656
```

<210> SEQ ID NO 14
<211> LENGTH: 1656
<212> TYPE: DNA
<213> ORGANISM: Artificial Sequence
<220> FEATURE:
<223> OTHER INFORMATION: Nucleotide sequence encoding a
      mutant(V288I+E488V)

<400> SEQUENCE: 14

```
atggaagacg ccaaaaacat aaagaaaggc ccggcgccat tctatcctct agaggatgga      60
accgctggag agcaactgca taaggctatg aagagatacg ccctggttcc tggaacaatt     120
```

| | |
|---|---|
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct aataccaacc ctatttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg aggggatga taaaccgggc | 1080 |
| gcggtcggta agttgttcc atttttgaa gcgaaggttg tggatctgga taccgggaaa | 1140 |
| acgctgggcg ttaatcagag aggcgaatta tgtgtcagag gacctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat ggaatcgat attgttacaa | 1380 |
| caccccaaca tcttcgacgc gggcgtggca ggtcttcccg acgatgacgc cggtgaactt | 1440 |
| cccgccgccc ttgttgtttt ggtgcacgga agacgatga cggaaaaaga gatcgtggat | 1500 |
| tacgtcgcca gtcaagtaac aaccgcgaaa agttgcgcg gaggagttgt gtttgtggac | 1560 |
| gaagtaccga aggtcttac cggaaaactc gacgcaagaa aaatcagaga gatcctcata | 1620 |
| aaggccaaga agggcggaaa gtccaaattg ctcgag | 1656 |

<210> SEQ ID NO 15
<211> LENGTH: 1656
<212> TYPE: DNA
<213> ORGANISM: Artificial Sequence
<220> FEATURE:
<223> OTHER INFORMATION: Nucleotide sequence encoding a
      mutant(V288I+L376P+E488V)

<400> SEQUENCE: 15

| | |
|---|---|
| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |

```
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct aataccaacc ctattttcat tcttcgccaa aagcactctg    900
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg aggggatga taaaccgggc   1080 gcggtcggta aagttgttcc attttttgaa gcgaaggttg tggatccgga taccgggaaa   1140
acgctgggcg ttaatcagag aggcgaatta tgtgtcagag gacctatgat tatgtccggt   1200
tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata tcaggtggcc cccgctgaat tggaatcgat attgttacaa   1380
caccccaaca tcttcgacgc gggcgtggca ggtcttcccg acgatgacgc cggtgaactt   1440
cccgccgccg ttgttgtttt ggtgcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gtccaaattg ctcgag                             1656
```

MUTANT BEETLE LUCIFERASE, GENE, RECOMBINANT VECTOR, TRANSFORMANT, AND METHOD FOR PREPARING MUTANT BEETLE LUCIFERASE

TECHNICAL FIELD

The present invention relates to a mutant beetle luciferase, a gene, a recombinant vector, a transformant, and a method for preparing such a mutant beetle luciferase.

This application claims the priority of Japanese Patent Application No. 2016-122545, filed Jun. 21, 2016, the contents of which are hereby incorporated.

BACKGROUND ART

Beetle luciferases are enzymes that catalyze the oxidation of firefly luciferins in the presence of adenosine triphosphate (ATP), magnesium ion, and oxygen, so as to bring about luminescences from the luciferins. Thus, the beetle luciferases and the luciferin-luciferase luminescence reaction using the same are broadly used for testing for the purpose of detecting microorganisms in a specimen using ATP as an index, such as ATP testing of microbial contamination and luminescence testing of endotoxin.

To enhance the availability of such beetle luciferases for detection of ATP, various mutant beetle luciferases have been prepared thus far. As such mutant beetle luciferases, beetle luciferases with improved thermostability (for example, see Patent Document 1), beetle luciferases with improved substrate affinity (for example, see Patent Document 2), beetle luciferases with altered luminescence wavelengths (for example, see Patent Document 3), beetle luciferases with improved luminescence continuity (for example, see Patent Document 4), beetle luciferases with resistance to surfactants (for example, see Patent Document 5), beetle luciferases with increased luminescence intensity (for example, see Patent Document 6) and the like are known.

PRIOR ART DOCUMENTS

Patent Documents

Patent Document 1: Japanese Patent No. 3048466
Patent Document 2: Japanese Translation of PCT International Application Publication No. JP-T-2001-518799
Patent Document 3: Japanese Patent No. 2666561
Patent Document 4: Japanese Unexamined Patent Application Publication No. 2000-197484
Patent Document 5: Japanese Unexamined Patent Application Publication No. 11-239493
Patent Document 6: Japanese Unexamined Patent Application Publication No. 2007-97577

SUMMARY

Technical Problem

In a wild-type beetle luciferase, an enzyme reaction is inhibited in an about 0.9% by mass aqueous sodium chloride solution, and a luminescence intensity is lowered to about 20 to 50% as compared with that in an aqueous solution containing no sodium chloride. Likewise, conventionally known mutant beetle luciferases as described in Patent Document 1-6 also decrease luminescence intensity in an about 0.9% by mass aqueous sodium chloride solution. Therefore, when a luciferin-luciferase luminescence reaction is carried out on a specimen containing sodium chloride at a physiological saline level such as dialysate or transfusion using these beetle luciferases, there remains a problem that the measurement sensitivity of ATP detection decreases due to luminescence inhibition by sodium chloride.

Therefore, an object of the present invention is to provide a mutant beetle luciferase which is less susceptible to luminescence inhibition by sodium chloride compared with those of a wild-type beetle luciferase.

Solution to Problem

As a result of intensive studies to achieve the objects, the present inventors have found that substitution of amino acids at specific positions in an amino acid sequence of a wild-type beetle luciferase with specific different amino acids suppresses the effect of luminescence inhibition by sodium chloride. Thus, the present inventors have completed the present invention.

Specifically, according to the present invention, the mutant beetle luciferase, the gene, the recombinant vector, the transformant, and the method for preparing such the mutant beetle luciferase are as the following items [1] to [13].

[1] A mutant beetle luciferase in which mutations have been introduced into a wild-type beetle luciferase,
the mutant beetle luciferase having one or more mutations selected from the group consisting of at least the following (a), (b), (c) and (d) in an amino acid sequence encoding the wild-type beetle luciferase, and
characterized in that a luminescence intensity due to a luciferin-luciferase luminescence reaction in a 0.9% by mass sodium chloride solution is 50% or more of that in a sodium chloride-free solution:
(a) mutation in which the amino acid corresponding to valine at position 288 in the amino acid sequence of wild-type *Photinus pyralis* luciferase is isoleucine, leucine, or phenylalanine;
(b) mutation in which the amino acid corresponding to leucine at position 376 in the amino acid sequence of wild-type *Photinus pyralis* luciferase is proline;
(c) mutation in which the amino acid corresponding to glutamic acid at position 455 in the amino acid sequence of wild-type *Photinus pyralis* luciferase is valine, alanine, serine, leucine, isoleucine or phenylalanine; and
(d) mutation in which the amino acid corresponding to glutamic acid at position 488 in the amino acid sequence of wild-type *Photinus pyralis* luciferase is valine, alanine, serine, leucine, isoleucine or phenylalanine.

[2] The mutant beetle luciferase according to item [1], wherein the wild-type beetle luciferase is wild-type *Photinus pyralis* luciferase.

[3] The mutant beetle luciferase according to item [1], wherein the wild-type beetle luciferase is wild-type *Luciola lateralis* luciferase,
wherein valine at position 288 in the amino acid sequence of the wild-type *Photinus pyralis* luciferase corresponds to valine at position 290 in the amino acid sequence of wild-type *Luciola lateralis* luciferase,
leucine at position 376 in the amino acid sequence of the wild-type *Photinus pyralis* luciferase corresponds to leucine at position 378 in the amino acid sequence of wild-type *Luciola lateralis* luciferase,
glutamic acid at position 455 in the amino acid sequence of the wild-type *Photinus pyralis* luciferase corresponds to glutamic acid at position 457 in the amino acid sequence of wild-type *Luciola lateralis* luciferase, and
glutamic acid at position 488 in the amino acid sequence of the wild-type *Photinus pyralis* luciferase corresponds to glutamic acid at position 490 in the amino acid sequence of wild-type *Luciola lateralis* luciferase.

[4] The mutant beetle luciferase according to item [1], wherein the wild-type beetle luciferase is wild-type *Luciola cruciata* luciferase,
wherein valine at position 288 in the amino acid sequence of the wild-type *Photinus pyralis* luciferase corresponds to valine at position 290 in the amino acid sequence of wild-type *Luciola cruciata* luciferase,
leucine at position 376 in the amino acid sequence of the wild-type *Photinus pyralis* corresponds to leucine at position 378 in the amino acid sequence of wild-type *Luciola cruciata* luciferase,
glutamic acid at position 455 in the amino acid sequence of the wild-type *Photinus pyralis* luciferase corresponds to glutamic acid at position 457 in the amino acid sequence of wild-type *Luciola cruciata* luciferase, and
glutamic acid at position 488 in the amino acid sequence of the wild-type *Photinus pyralis* luciferase corresponds to glutamic acid at position 490 in the amino acid sequence of wild-type *Luciola cruciata* luciferase.

[5] The mutant beetle luciferase of item [1], wherein the wild-type beetle luciferase is wild-type *Pyrophorus plagiophthalamus* luciferase,
the mutant beetle luciferase having one or more mutations selected from the group consisting of at least (a), (c) and (d) in the amino acid sequence encoding the wild-type beetle luciferase, and
wherein valine at position 288 in the amino acid sequence of the wild-type *Photinus pyralis* luciferase corresponds to valine at position 285 in the amino acid sequence of wild-type *Pyrophorus plagiophthalamus* luciferase,
glutamic acid at position 455 in the amino acid sequence of the wild-type *Photinus pyralis* luciferase corresponds to glutamic acid at position 452 in the amino acid sequence of wild-type *Pyrophorus plagiophthalamus* luciferase, and
glutamic acid at position 488 in the amino acid sequence of the wild-type *Photinus pyralis* luciferase corresponds to glutamic acid at position 489 in the amino acid sequence of wild-type *Pyrophorus plagiophthalamus* luciferase.

[6] The mutant beetle luciferase of any one of the preceding items, having the mutations of (a) and (d).

[7] The mutant beetle luciferase any one of items [1] to [4], having the mutations having two or more mutations selected from the group consisting of (a), (b) and (d).

[8] The mutant beetle luciferase any one of the preceding items, wherein the mutations of (a), (c) and (d) are the following (a'), (c') and (d'), respectively:
(a') mutation in which the amino acid corresponding to valine at position 288 in the amino acid sequence of wild-type *Photinus pyralis* luciferase is isoleucine;
(c') mutation in which the amino acid corresponding to glutamic acid at position 455 in the amino acid sequence of wild-type *Photinus pyralis* luciferase is valine; and
(d') mutation in which the amino acid corresponding to glutamic acid at position 488 in the amino acid sequence of wild-type *Photinus pyralis* luciferase is valine.

[9] The mutant beetle luciferase according to any one of the preceding items, wherein the luminescence intensity due to the luciferin-luciferase luminescence reaction in the 0.9% by mass sodium chloride solution is greater than that of the wild-type beetle luciferase.

[10] A gene encoding the mutant beetle luciferase of any one of the preceding items.

[11] A recombinant vector containing the gene according to item [10].

[12] A transformant having the recombinant vector according to item [11].

[13] A method for preparing a mutant beetle luciferase, comprising steps of culturing the transformant according to item [12] to obtain a culture and collecting the mutant beetle luciferase from the culture obtained in the culturing step.

Advantageous Effects of Invention

According to the present invention, a mutant beetle luciferase which is less susceptible to luminescence inhibition by sodium chloride compared with a wild-type beetle luciferase is provided. Performing the luciferin-luciferase luminescence reaction using the mutant beetle luciferase makes it possible to perform ATP detection of a specimen whose sodium chloride concentration is equivalent to physiological saline with high sensitivity.

Further, using the gene, recombinant vector, transformant according to the present invention and the method for preparing the mutant beetle luciferase, makes it possible to efficiently prepare the mutant beetle luciferase according to the present invention.

DESCRIPTION OF EMBODIMENTS

Figure 1:
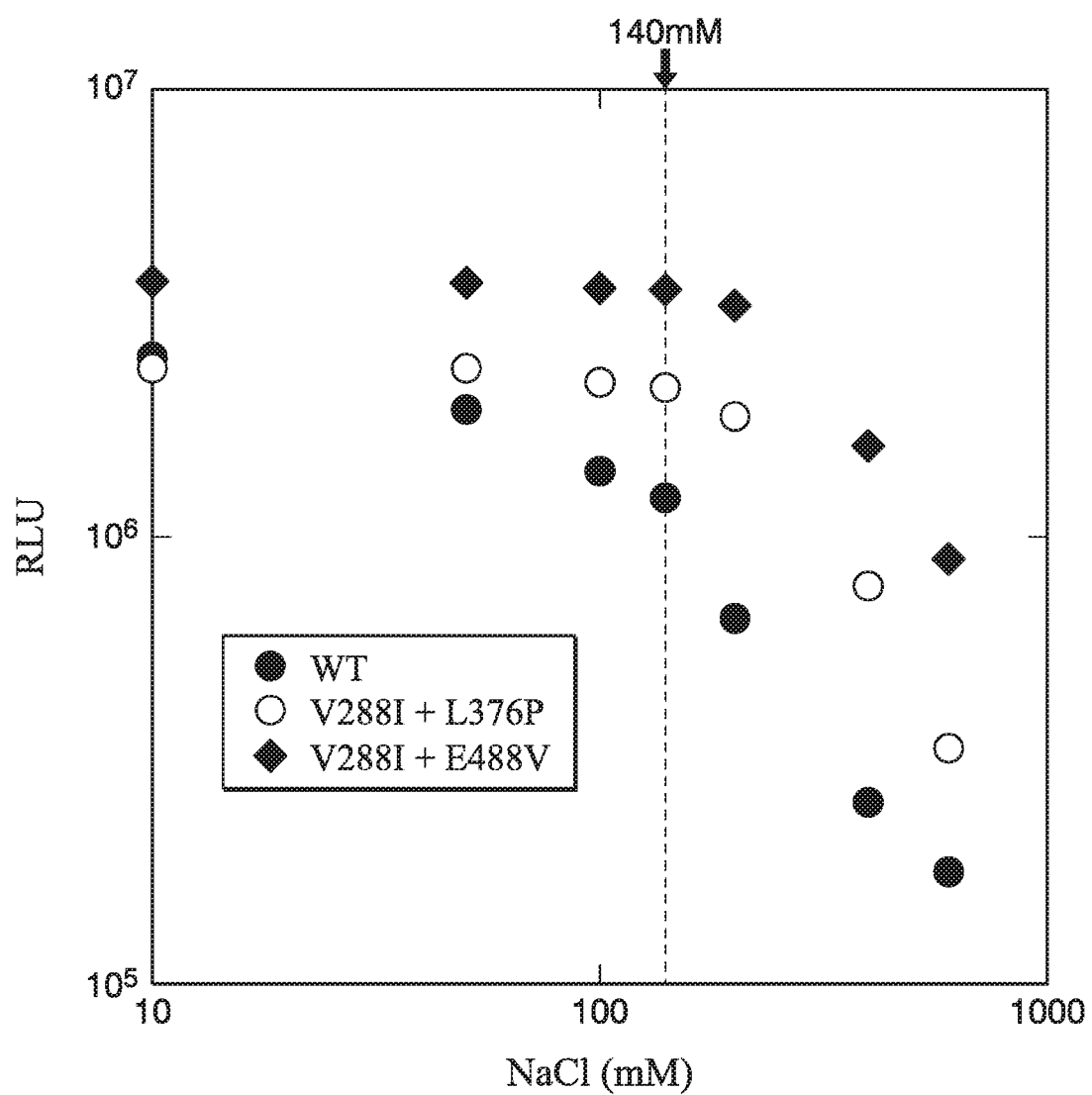
FIG. 1 is a plot diagram of measurement values of luminescence intensity (RLU) of each beetle luciferase for each sodium chloride concentration (mM) in the reaction solution in Example 2.

In the present invention and the present specification, "luminescence intensity" of beetle luciferase means, unless otherwise specified, peak luminescence intensity in a luciferin-luciferase luminescence reaction, that is, peak luminescence intensity when the beetle luciferase is caused to react with firefly luciferin in the presence of ATP, a divalent metal ion, and oxygen. In addition, it can be concluded that the larger the "luminescence intensity", the stronger luciferase activity of the beetle luciferase.

In the present specification, "residual activity (%)" of beetle luciferase refers to the relative value ([a luminescence intensity in a 0.9% by mass sodium chloride solution]/[a luminescence intensity in a sodium chloride-free solution]× 100) (%) of the luminescence intensity in a 0.9% by mass sodium chloride solution, when the luminescence intensity in a sodium chloride-free solution is taken as 100%. Here, the reaction solution of the luciferin-luciferase luminescence reaction being "sodium chloride-free solution" refers to the reaction solution that was prepared without incorporating sodium chloride. When performing the luciferin-luciferase luminescence reaction to calculate the residual activity, compositions of "sodium chloride-free solution" and "0.9% by mass sodium chloride solution" are all the same except for sodium chloride, and the reaction is carried out under the same reaction conditions such as reaction temperature and time Mutant Beetle Luciferase The mutant beetle luciferase according to the present invention is a wild-type beetle luciferase in which mutations have been introduced and a luminescence intensity in a 0.9% by mass sodium chloride solution is 50% or more of that in a sodium chloride-free solution. The luciferase activity of the mutant beetle luciferase according to the present invention may be a residual activity of 50% or more, preferably 60% or more, more preferably 70% or more, further preferably 80% or more, and even more preferably 90% or more.

Like a wild-type beetle luciferase, the mutant beetle luciferase according to the present invention can be used for a luciferin-luciferase luminescence reaction, and since it is not susceptible to luminescence inhibition by sodium chloride, it is particularly suitable as a beetle luciferase used for a luciferin-luciferase luminescence reaction to a specimen containing sodium chloride. For example, when a luciferin-luciferase luminescence reaction is carried out to measure the amount of ATP for the purpose of detecting microorganisms on infusion or dialysis solution administered to a specimen collected from an animal such as a human and a human itself, the use of the mutant beetle luciferase according to the present invention makes it possible to perform ATP detection with higher sensitivity.

The mutant beetle luciferase according to the present invention has one or more mutations selected from the group consisting of at least the following (a), (b), (c) and (d) in an amino acid sequence encoding the wild-type beetle luciferase: (a) mutation in which the amino acid corresponding to valine at position 288 in the amino acid sequence of wild-type *Photinus pyralis* luciferase is isoleucine, leucine, or phenylalanine;
(b) mutation in which the amino acid corresponding to leucine at position 376 in the amino acid sequence of wild-type *Photinus pyralis* luciferase is proline;
(c) mutation in which the amino acid corresponding to glutamic acid at position 455 in the amino acid sequence of wild-type *Photinus pyralis* luciferase is valine, alanine, serine, leucine, isoleucine or phenylalanine; and
(d) mutation in which the amino acid corresponding to glutamic acid at position 488 in the amino acid sequence of wild-type *Photinus pyralis* luciferase is valine, alanine, serine, leucine, isoleucine or phenylalanine.

In the present invention and the present specification, "wild-type beetle luciferase" includes *Photinus pyralis* luciferase (SEQ ID NO:1), *Luciola lateralis* luciferase (SEQ ID NO:2), *Luciola cruciata* luciferase (SEQ ID NO:3), *Luciola mingrelica* luciferase, *Lampyris noctiluca* luciferase, *Pyrophorus plagiophthalamus* luciferase (SEQ ID NO:4) or the like. Further, the amino acid sequences of various wild-type beetle luciferases can be searched in a database (e.g., EMBL-EBI Database (ebi.ac.uk/queries/)).

When a wild-type beetle luciferase is not *Photinus pyralis* luciferase, "the amino acid corresponding to the amino acid at position X in the amino acid sequence of *Photinus pyralis* luciferase" in the amino acid sequence of the wild-type beetle luciferase means the amino acid at the position corresponding to "the amino acid at position X in the amino acid sequence of *Photinus pyralis* luciferase", when aligning the amino acid sequences of the wild-type beetle luciferase and *Photinus pyralis* luciferase so that they have the highest homology using software for analysis of amino acid sequence homology (e.g., Micro Genie™ (produced by Beckman Coulter, Inc.)) or the like.

Specifically, the amino acid corresponding to valine at position 288 in the amino acid sequence of wild-type *Photinus pyralis* luciferase corresponds to valine at position 290 in the amino acid sequence of wild-type *Luciola lateralis* luciferase, valine at position 290 in the amino acid sequence of wild-type *Luciola cruciata* luciferase, valine at position 285 in the amino acid sequence of wild-type *Pyrophorus plagiophthalamus* luciferase, respectively. Leucine at position 376 in the amino acid sequence of wild-type *Photinus pyralis* luciferase corresponds to leucine at position 378 in the amino acid sequence of wild-type *Luciola lateralis* luciferase, leucine at position 378 in the amino acid sequence of wild-type *Luciola cruciata* luciferase, respectively. Glutamic acid at position 455 in the amino acid sequence of wild-type *Photinus pyralis* luciferase corresponds to glutamic acid at position 457 in the amino acid sequence of wild-type *Luciola lateralis* luciferase, glutamic acid at position 457 in the amino acid sequence of wild-type *Luciola cruciata* luciferase, glutamic acid at position 452 in the amino acid sequence of wild-type *Pyrophorus plagiophthalamus* luciferase, respectively. Glutamic acid at position 488 in the amino acid sequence of wild-type *Photinus pyralis* luciferase corresponds to glutamic acid at position 490 in the amino acid sequence of wild-type *Luciola lateralis* luciferase, glutamic acid at position 490 in the amino acid sequence of wild-type *Luciola cruciata* luciferase, glutamic acid at position 489 in the amino acid sequence of wild-type *Pyrophorus plagiophthalamus* luciferase, respectively.

When the mutant beetle luciferase according to the present invention has the mutation of (a), the amino acid corresponding to valine at position 288 in the amino acid sequence of wild-type *Photinus pyralis* luciferase is preferably isoleucine or leucine, more preferably isoleucine, as the mutation.

When the mutant beetle luciferase according to the present invention has the mutation of (c), the amino acid corresponding to glutamic acid at position 455 in the amino acid sequence of wild-type *Photinus pyralis* luciferase is preferably valine, leucine, isoleucine or alanine, more preferably valine, as the mutation.

When the mutant beetle luciferase according to the present invention has the mutation of (d), the amino acid corresponding to glutamic acid at position 488 in the amino acid sequence of wild-type *Photinus pyralis* luciferase is preferably valine, leucine, isoleucine or alanine, more preferably valine, as the mutation.

The mutant beetle luciferase according to the present invention may have only one of or in combination of two or more of the mutations of (a), (b), (c) and (d). Particularly, among the mutations of (a), (b), (c) and (d), the mutant beetle luciferase having only the mutation of (a), the mutant beetle luciferase having only the mutation of (b), the mutant beetle luciferase having only the mutation of (d), the mutant beetle luciferase having the mutations of (a) and (b), the mutant beetle luciferase having mutations of (a) and (d), or the mutant beetle luciferase having the mutations of (a), (b) and (d) is preferred, because the luminescence intensity due to the luciferin-luciferase luminescence reaction in a 0.9% by mass sodium chloride solution is greater than that of the wild-type beetle luciferase. Furthermore, among the mutations of (a), (b), (c) and (d), the mutant beetle luciferase having only the mutation of (a), the mutant beetle luciferase having only the mutation of (d), the mutant beetle luciferase having the mutations of (a) and (b), the mutant beetle luciferase having mutations of (a) and (d), or the mutant beetle luciferase having the mutations of (a), (b) and (d) is more preferred, because the residual activity is also high.

The mutant beetle luciferase according to the present invention includes, for example, the mutant beetle luciferase in which the amino acid corresponding to valine at position 288 in the amino acid sequence of wild-type *Photinus pyralis* luciferase is substituted with isoleucine, the mutant beetle luciferase in which the amino acid corresponding to leucine at position 376 in the amino acid sequence of wild-type *Photinus pyralis* luciferase is substituted with a proline, the mutant beetle luciferase in which the amino acid corresponding to glutamic acid at position 455 in the amino acid sequence of wild-type *Photinus pyralis* luciferase is substituted with the valine, the mutant beetle luciferase in which the amino acid corresponding to glutamic acid at position 488 in the amino acid sequence of wild-type *Photinus pyralis* luciferase is substituted with valine, the mutant beetle luciferase in which the amino acid corresponding to valine at position 288 and leucine at position 376 in the amino acid sequence of wild-type *Photinus pyralis* luciferase is substituted with isoleucine and proline, respectively, the mutant beetle luciferase in which the amino acid corresponding to valine at position 288 and glutamic acid at position 488 in the amino acid sequence of wild-type *Photinus pyralis* luciferase is substituted with isoleucine and valine, respectively, the mutant beetle luciferase in which an amino acid corresponding to a valine at position 288, a leucine at position 376 and glutamic acid at position 488 in the amino acid sequence of wild-type *Photinus pyralis* luciferase is substituted with isoleucine, proline and valine, respectively, and the like.

The mutant beetle luciferase according to the present invention has improved salt tolerance by having at least one of mutations of (a), (b), (c) and (d), and the luciferase activity of the mutant beetle luciferase is less inhibited by sodium chloride than that of the wild-type beetle luciferase. The reason why salt tolerance was improved by these specific mutations is not clear, but it is surmised that the introduction of amino acid substitution along with change in molecular size and charge at these specific positions changed the conformation near the active center in the enzyme reaction of the beetle luciferase and suppressed sodium ions from entering the reaction site that inhibits the oxidation reaction of luciferin.

The mutant beetle luciferase according to the present invention may be identical to the amino acid sequence of the wild-type beetle luciferase except for the mutation of (a), (b), (c) and (d), and have other mutations than the mutation described in (a) or the like, relative to the amino acid sequence of the wild-type beetle luciferase. The other mutations include, but not limited to, those which do not impair luciferase activity and salt tolerant effect due to the mutations such as (a), for example, the mutations described in Patent Document 1 to 6.

The mutant beetle luciferase according to the present invention includes proteins such as the following (1) to (3):
(1) the protein consisting of the amino acid sequence in which one or more mutations selected from the group consisting of (a), (b), (c) and (d) have been introduced into the amino acid sequence of the wild-type beetle luciferase;
(2) the protein consisting of the amino acid sequence which has one or more mutations selected from the group consisting of (a), (b), (c) and (d), and mutations of deletion, substitution or addition of one or more amino acids in the amino acid sequence of the wild-type beetle luciferase, and having luciferase activity; and (3) the protein consisting of the amino acid sequence which has 80% or more sequence identity with the amino acid sequence of the wild-type beetle luciferase, and one or more mutations selected from the group consisting of (a), (b), (c) and (d), and having luciferase activity.

In the protein of (2), except for the mutations of (a), (b), (c) and (d), the number of amino acids deleted, substituted or added to the amino acid sequence of the wild-type beetle luciferase is preferably 1-20, more preferably 1-10, even preferably 1-5.

In the protein of (3), the sequence identity with the amino acid sequence of the wild-type beetle luciferase is not particularly limited as long as it is 80% or more and less than 100%, but preferably 85% or more and less than 100%, more preferably 90% or more and less than 100%, even preferably 95% or more and less than 100%, even more preferably 98% or more and less than 100%.

Further, the sequence identity (homology) between amino acid sequences is determined by aligning two amino acid sequences with gaps in the insertion and deletion portions so that the corresponding amino acids correspond most frequently, and calculating the proportion of matched amino acids to the entire amino acid sequence excluding the gap in the resulting alignment. The sequence identity between amino acid sequences can be determined using various homology search software known in the art.

In the mutant beetle luciferase according to the present invention, various tags may be added to N or C terminus of a region having luciferase activity. As the tag, for example, a tag widely used in expression/purification of a recombinant protein such as histidine tag, HA (hemagglutinin) tag, Myc tag, Flag tag or the like can be used. Mutant beetle luciferase gene A gene encoding the mutant beetle luciferase according to the present invention (mutant beetle luciferase gene) can be provided by modifying a wild-type beetle luciferase gene appropriately. The mutant beetle luciferase gene according to the present invention may be one obtained by modifying a codon encoding a corresponding amino acid so that a mutation is introduced into the wild-type beetle luciferase gene, furthermore one in which a degenerate codon has been modified to have high codon usage frequency of a host.

In the present invention and the present specification, "gene" consists of DNA or RNA and refers to a polynucleotide encoding a protein. In addition, genetic modification can be performed by methods well known to those skilled in the art such as site-directed mutagenesis, random mutagenesis, organic synthesis.

Site-directed mutagenesis or random mutagenesis is carried out using the wild-type beetle luciferase gene or a recombinant vector containing the same as a template. The wild-type beetle luciferase gene or the recombinant vector containing the same can be prepared by methods well known to those skilled in the art (methods described in, for example, "Genetic engineering laboratory notebook" (Yodosha), Japanese Unexamined Patent Application Publication No. 1-51086, Japanese Patent No. 3048466 and the like). Additionally, commercially available ones may also be employed.

Site-directed mutagenesis can be carried out by methods well known to those skilled in the art, such as a method of synthesizing with T4 DNA polymerase using a selection primer and a mutagenic primer and the like. When site-directed mutagenesis is carried out using a recombinant vector containing a wild-type beetle luciferase gene as a template and using a selection primer and a mutagenic primer, the recombinant vector into which the mutation has not been introduced can be selectively removed by cutting treatment with the corresponding restriction enzyme, for example, since the restriction enzyme recognition sequence is directly present in the recombinant vector into which the mutation has not been introduced when a DNA fragment containing the sequence different from the restriction enzyme recognition sequence present in the recombinant vector by one base is used as a selection primer.

Random mutagenesis can be performed by methods well known to those skilled in the art, such as a method that involves lowering fidelity by the addition of manganese and dGTP and then performing polymerase chain reaction (PCR), a method that involves causing a drug (e.g., hydroxylamine, N-methyl-N'-nitro-N-nitrosoguanidine and the like) to come into contact, and a method that involves UV irradiation. When random mutagenesis is performed, a target mutant beetle luciferase gene or a recombinant vector containing the gene can be selected through determination of the nucleotide sequence of a gene into which mutation has been introduced.

The nucleotide sequence of a gene into which mutation has been introduced can be determined by methods well known to those skilled in the art, such as a dideoxy chain termination method. In addition, a database (e.g., EMBL Nucleotide Sequence Database (ebi.ac.uk/embl/)) can be searched for the nucleotide sequences of various wild-type beetle luciferase genes (cDNAs).

Recombinant Vector

The recombinant vector according to the present invention contains the mutant beetle luciferase gene according to the present invention.

The recombinant vector can be obtained according to methods well known to those skilled in the art, which involves inserting the mutant beetle luciferase gene according to the present invention into a vector (e.g., a plasmid and a bacteriophage) replicable within host cells. Such insertion of the mutant beetle luciferase gene into a vector can be performed by digesting a DNA fragment which was prepared by addition of an appropriate restriction enzyme recognition sequence to the mutant beetle luciferase gene using the corresponding restriction enzyme and then ligating the obtained gene fragment to the vector via its insertion to the corresponding restriction enzyme recognition sequence or the multi-cloning site in the vector.

The recombinant vector can also be obtained, as described above, by introducing mutation into a recombinant vector containing a wild-type beetle luciferase gene.

Examples of a plasmid include plasmids derived from *Escherichia coli* (e.g., pET28a(+), pGL2, pBR322, pUC18, pTrcHis, and pBlueBacHis), plasmids derived from *Bacillus subtilis* (e.g., pUB110 and pTP5), and plasmids derived from yeast (e.g., YEp13, YEp24, YCp50, and pYE52). Examples of a bacteriophage include λphage and the like.

The recombinant vector according to the present invention is preferably capable of expressing a mutant beetle luciferase utilizing an expression system of a host cell when introduced into the host cell. Therefore, the recombinant vector according to the present invention is preferably incorporated as an expression cassette in which an appropriate promoter functioning in the host cell is arranged upstream of the mutant beetle luciferase gene according to the present invention. If necessary, enhancers, terminators, splicing signals, poly A addition signals, ribosome binding sequences (SD sequences) and the like can be placed in the expression cassette.

In the expression cassette of the mutant beetle luciferase, the promoter sequence arranged upstream of the mutant beetle luciferase gene may be a promoter derived from the same organism species as the wild-type beetle luciferase gene before mutation is introduced, may be a promoter derived from heterologous species, or may be an artificially synthesized promoter. For example, when *E. coli* is used as a host cell, the promoters that control an expression of the mutant beetle luciferase gene include trp promoter, lac promoter, T7 promoter, PL promoter, PR promoter and the like.

The recombinant vector according to the present invention preferably also contains a selectable marker gene for selecting a transformed cell and a non-transformed cell, in addition to the expression cassette of the mutant beetle luciferase. The selectable marker gene includes drug resistance gene such as kanamycin resistance gene, hygromycin resistance gene, and bialaphos resistance gene.

Reporter assay can be performed with sufficiently high sensitivity through the use of the mutant beetle luciferase gene according to the present invention as a reporter gene. Such reporter assay becomes possible by the use of the recombinant vector according to the present invention containing the mutant beetle luciferase gene.

Transformant

The transformant according to the present invention has the recombinant vector according to the present invention.

The transformant according to the present invention can be obtained according to methods well known to those skilled in the art, which involves introducing the recombinant vector into a host cell. Introduction of the recombinant vector into the host cell can be performed by methods well known to those skilled in the art, such as a calcium chloride method, an electroporation method, a polyethylene glycol method, a lipofection method, and a particle gun method.

Host cells include bacteria such as *Escherichia coli*, *Bacillus subtilis*, yeast such as *Saccharomyces cerevisiae*, filamentous fungi such as *Aspergillus* spp., insect cells such as Sf9 cells and Sf21 cells, and mammal cells such as COS cells and CHO cells, and the like. The transformant according to the present invention is preferably obtained using *Escherichia coli* as a host because it is fast growing and easy to handle.

Method for Preparing Mutant Beetle Luciferase

A method for preparing the mutant beetle luciferase according to the present invention comprises steps of culturing the transformant according to the present invention to obtain a culture, and collecting the mutant beetle luciferase from the culture obtained in the culturing step. The mutant beetle luciferase according to the present invention can be obtained by the method for preparing.

The culturing step is the step of culturing the transformant according to the present invention to obtain a culture. As used herein, "culture" may be any of culture supernatant, culture cells and disrupted cells.

The transformant can be cultured by methods well known to those skilled in the art. For example, when the host cell is a microorganism such as *Escherichia coli* and yeast, the media used for culturing the transformant may contain a carbon source (such as glucose, sucrose, lactose), a nitrogen source (such as peptone, meat extract, Yeast extract), inorganic salts (such as phosphate, carbonate, sulfate) assimilable by the microorganism and the like. When the media is one in which the host cells can be efficiently cultured, it can be either natural media or chemically defined media, or it can be either liquid media or solid media. Which of shaking culture, stirred culture, standing culture and the like is to be carried out and the other culture conditions (culturing temperature, pH of the media, culturing time, etc.) can be appropriately decided according to the host cell, culture media and the like to be used. For example, when the host cell is *Escherichia coli*, the culturing temperature is generally from 30 to 42° C., preferably 37° C. The pH of the media is generally from 6.4 to 8.0, preferably from 7.0 to 7.4. When the culturing temperature is 37° C., the culturing time of the preculture is generally 8 to 20 hours, preferably 12 to 16 hours, and the culturing time of the main culture before induction of expression is generally 2 to 8 hours, preferably 2 to 4 hours. However, the optimal culturing time is determined depending on the culturing temperature and the pH of the media.

If necessary, expression inducers can be added to the medium. Such expression inducers include, for example, isopropyl β-thiogalactoside (IPTG) and the like when the recombinant vector contains the lac promoter, and indole acrylic acid (IAA) and the like when the recombinant vector contains trp promoter.

When the recombinant vector is prepared using the vector which has a resistance to antibiotics (such as kanamycin, ampicillin), antibiotic resistance can be used as a selectable marker for the transformant by adding the antibiotics to the media.

The collecting step is a step of collecting the mutant beetle luciferase according to the present invention from a culture obtained in the culturing step The mutant beetle luciferase can be collected from the transformant by methods well known to those skilled in the art, such as the method in which the transformant is collected from the culture by centrifugation and the resulting transformant is subjected to freeze-thaw treatment, ultrasonic fragmentation treatment, or treatment with a lytic enzyme such as lysozyme. Further, the mutant beetle luciferase may be collected in the state of solution.

In the method for preparing, after the collecting step, a purification step of purifying the mutant beetle luciferase (crude enzyme) obtained in the collecting step may be further carried out. A crude enzyme can be purified by performing for example, ammonium sulfate precipitation, SDS-PAGE, gel filtration chromatography, ion exchange chromatography, affinity chromatography and the like singly or in combination arbitrarily.

EXAMPLES

Hereinafter, the present invention will be illustrated by examples, but the present invention is not limited by the following Examples.

Example 1

Mutant *Photinus pyralis* luciferase in which valine at position 288 in the amino acid sequence of wild-type *Photinus pyralis* luciferase is substituted with isoleucine (the mutant (V288I)), mutant *Photinus pyralis* luciferase in which leucine at position 376 in the amino acid sequence of wild-type *Photinus pyralis* luciferase is substituted with proline (the mutant (L376P)), mutant *Photinus pyralis* luciferase in which glutamic acid at position 455 in the amino acid sequence of wild-type *Photinus pyralis* luciferase is substituted with valine (the mutant (E455V)), mutant *Photinus pyralis* luciferase in which glutamic acid at position 488 in the amino acid sequence of wild-type *Photinus pyralis* luciferase is substituted with valine (the mutant (E488V)), mutant *Photinus pyralis* luciferase in which valine at position 288 and leucine at position 376 in the amino acid sequence of wild-type *Photinus pyralis* luciferase is substituted with isoleucine and proline, respectively (the mutant (V288I+L376P)), mutant *Photinus pyralis* luciferase the in which valine at position 288 and glutamic acid at position 488 in the amino acid sequence of wild-type *Photinus pyralis* luciferase is substituted with isoleucine and valine, respectively (the mutant (V288I+E488V)), mutant *Photinus pyralis* luciferase in which valine at position 288, leucine at position 376 and glutamic acid at position 488 in the amino acid sequence of wild-type *Photinus pyralis* luciferase is substituted with isoleucine, proline and valine, respectively (the mutant (V288I+L376P+E488V)) were prepared, and those luciferase activities (luminescence intensity) were measured.

Preparation of a Recombinant Vector Containing Mutant *Photinus pyralis* Luciferase Gene First, PCR was performed using a recombinant plasmid having wild-type *Photinus pyralis* luciferase gene (cDNA) (SEQ ID NO: 5) integrated into a commercially available plasmid (pGL2-Basic Vector (Promega KK)) as a template, a primer (5'-gactccatggaagacgccaaaaac-3', SEQ ID NO: 6) containing a recognition sequence of restriction enzyme Nco I, a primer (5'-gacactcgagcaatttggactttccgcc-3', SEQ ID NO: 7) containing a recognition sequence of restriction enzyme XhoI, and TITANIUM Taq DNA polymerase (produced by Clontech). Thus, a DNA fragment containing wild-type *Photinus pyralis* luciferase gene having a recognition sequence of a restriction enzyme added to both ends was obtained. The nucleotide sequence of the obtained DNA fragment was determined using a DTCS Quick Start Master Mix kit and electrophoresis analysis apparatus CEQ8000 (both produced by Beckman Coulter). The DNA fragment was cleaved with restriction enzyme Nco I and Xho I. The resultant was then incorporated into a plasmid (pET-28a(+) plasmid DNA (produced by Novagen)) that had been cleaved with Nco I and Xho I in advance using a DNA Ligation Kit (produced by BioDynamics Laboratory). Thus, a recombinant vector to express wild-type *Photinus pyralis* luciferase having a histidine tag which was added to the C-terminal side was prepared. In addition, pET-28a(+) is a vector that contains a T7 promoter and a T7 terminator and a gene encoding a histidine tag in the vicinity of the cloning site, so that the histidine tag was added to the C-terminal side of the target protein to be expressed.

Next, site-directed mutagenesis was performed using the obtained recombinant vector as a template and a Transformer site-directed mutagenesis kit (produced by Clontech). A selection primer used herein was a primer (5'-cacgatcatgagcacccgtgg-3', SEQ ID NO: 8) containing a base sequence differing from restriction enzyme Fsp I recognition sequence in pET-28a(+) by one base. In addition, the 5' ends of the selection primer and the mutagenic primer to obtain genes for each mutant had been phosphorylated in advance with T4 polynucleotide kinase (produced by TOYOBO).

A recombinant plasmid was synthesized using T4 DNA polymerase and T4 DNA ligase provided with a Transformer site-directed mutagenesis kit. After cleavage treatment of the reactant after the ligase reaction with restriction enzyme Fsp I, recombinant plasmids that had not been cleaved with Fsp I were introduced into *Escherichia coli* mismatch repair deficient strain BMH71-18mutS, followed by culturing of *Escherichia coli*. The obtained recombinant plasmid was further cleaved with Fsp I, and the recombinant vector that had not been cleaved with Fsp I were selected as the recombinant plasmid into which mutation had been introduced.

The base sequence of mutant *Photinus pyralis* luciferase gene (DNA) in the recombinant vector into which mutation had been introduced was determined using a DTCS Quick Start Master Mix kit and an electrophoresis analysis apparatus CEQ8000 (both produced by Beckman Coulter). As a result, the recombinant vector into which a gene encoding the mutant of interest had been incorporated was prepared. The base sequence encoding the mutant (V288I) is shown in SEQ ID NO:9, the base sequence encoding the mutant (L376P) is shown in SEQ ID NO:10, the base sequence encoding the mutant (E455V) is shown in SEQ ID NO:11, the base sequence encoding the mutant (E488V) is shown in SEQ ID NO:12, the base sequence encoding the mutant (V288I+L376P) is shown in SEQ ID NO:13, the base sequence encoding the mutant (V288I+L488V) is shown in SEQ ID NO:14, and the base sequence encoding the mutant (V288I+L376P+L488V) is shown in SEQ ID NO:15, respectively.

Preparation of Transformed *Escherichia coli*

The recombinant vector containing each mutant *Photinus pyralis* luciferase gene was introduced by a calcium chloride method into *Escherichia coli* (HMS174 (DE3) (produced by Novagen)) having genomic DNA into which a T7 RNA polymerase gene had been incorporated. The *Escherichia coli* was subjected to plate culture on selection agar medium containing 30 µg/mL kanamycin, so that transformed *Escherichia coli* was selected.

Collection and Purification of Mutant *Photinus pyralis* Luciferase

Kanamycin selected transformed *Escherichia coli* was subjected to shake culture for 2.5 hours using a shake culture system (produced by Takasaki Scientific Instrument Co., Ltd.) at 37° C. in 200 mL of 2×YT medium (containing 30 µg/mL kanamycin). 200 µL of 100 mM IPTG was then added so that the IPTG concentration in the medium reached 0.1 mM, followed by 6 hours of expression induction at 25° C. In addition, IPTG is an expression inducer that cancels the expression suppressed due to a lac repressor and induces T7 RNA polymerase.

Microbial bodies of *Escherichia coli* were collected by subjecting the culture solution to 5 minutes of centrifugation at 8000 rpm. The resultant was frozen at −20° C. and then preserved. The frozen microbial bodies were thawed with 5 mL of a binding buffer (20, mM NaH$_2$PO$_4$ (pH 7.4) containing 500 mM NaCl and 20 mM imidazole), suspended, and then disrupted by ultrasound. The obtained solution containing disrupted microbial bodies was centrifuged at 9000 rpm for 30 minutes. Thus, a supernatant as mutant *Photinus pyralis* luciferase (crude enzyme) solution was collected.

A histidine tag had been added to the C-terminal side of the thus expressed mutant firefly luciferase. Hence, a crude enzyme was purified by nickel chelate affinity chromatography. First, a column (produced by PIERCE, Disposable Polystyrene Column) was filled with 0.5 mL of Ni Sepharose 6 Fast Flow (produced by Amersham Biosciences), followed by equilibration using a binding buffer. Next, 5 mL of a crude enzyme solution was added to the column and the resultant was washed with a binding buffer. Then, mutant *Photinus pyralis* luciferase was eluted with 2.5 mL of an elution buffer (20 mM NaH$_2$PO$_4$ (pH 7.4) containing 500 mM NaCl and 500 mM imidazole). Furthermore, with the use of a PD-10 Desalting column (produced by Amersham Biosciences), the elution buffer was substituted with 3.5 mL of a reaction buffer (50 mM Tris-HCl buffer (pH 7.4) containing 10 mM MgCl$_2$). The purified mutant *Photinus pyralis* luciferase was thus obtained.

Measurement of the Luminescence Intensity of Mutant *Photinus pyralis* Luciferase Protein quantification for the obtained mutant *Photinus pyralis* luciferase was performed using Bio-Rad Protein Assay (produced by BIORAD) based on the Bradford method and IgG as a standard. 50 µL of a reaction buffer containing the mutant *Photinus pyralis* luciferase (20 µg/mL) was added to a 96-well plate (produced by Nunc, LumiNunc plate). Subsequently, 50 µL of a sodium chloride-containing substrate buffer (1.8% by mass sodium chloride, 50 mM Tris-HCl buffer (pH 7.4) containing 2×10$^{-6}$M D-firefly luciferin (produced by Wako Pure Chemical Industries, Ltd.), 2×10$^{-7}$M ATP, and 10 mM MgCl$_2$) or 50 µL of a sodium chloride-free substrate buffer (50 mM Tris-HCl buffer (pH 7.4) containing 2×10$^{-6}$M D-firefly luciferin (produced by Wako Pure Chemical Industries, Ltd.), 2×10$^{-7}$M ATP, and 10 mM MgCl$_2$) was added using an injector provided with a microplate reader (produced by Perkin-Elmer, ARVO MX). Then, luminescence intensity was measured using the above microplate reader. The final concentration of sodium chloride in the reaction solution to which the sodium chloride-containing substrate buffer was added was 0.9% by mass. Also for wild-type *Photinus pyralis* luciferase, transformed *Escherichia coli* was prepared in a manner similar to that employed for the mutant *Photinus pyralis* luciferase, except that a recombinant vector containing wild-type *Photinus pyralis* luciferase gene (cDNA) was used instead of the recombinant vector containing the mutant *Photinus pyralis* luciferase gene. The enzyme was collected and purified and then the luminescence intensity of the enzyme was measured.

For the wild-type and each mutant, the residual activity (%) was calculated from the measurement value of luminescence intensity. The calculated results are provided in Table 1. In Table 1, the column "No NaCl" shows the measurement value of luminescence intensity of the reaction solution containing no sodium chloride, and the column "+0.9% NaCl" shows the measurement value of luminescence intensity (Relative Light Unit; RLU)) of the reaction solution containing 0.9% by mass sodium chloride.

TABLE 1

| luciferase | RLU | | residual activity |
| --- | --- | --- | --- |
| | No NaCl | +0.9% NaCl | (%) |
| WT | 569,480 | 247,299 | 43.4 |
| V288I | 622,173 | 390,783 | 62.8 |
| L376P | 555,480 | 290,940 | 52.4 |
| E455V | 279,420 | 173,655 | 62.1 |
| E488V | 575,161 | 407,182 | 70.8 |
| 288I + L376P | 887,085 | 786,012 | 88.6 |
| 288I + E488V | 931,439 | 894,868 | 96.1 |
| 288I + L376P + E488V | 927,447 | 873,800 | 94.2 |

As a result, in the wild-type, the residual activity was as very low as about 40%, and the luminescence inhibition by sodium chloride was large, whereas in any mutants the residual activity was 50% or more, the salt tolerance was improved more than that of the wild-type. Among them, in the mutant into which mutations have been introduced at positions 288, 376, or 488, the luminescence intensity in the presence of 0.9% by mass sodium chloride is stronger than that of the wild-type and luciferase activity is high. In particular, the residual activity of the mutant (V288I+L376P), the mutant (V288I+E488V) and the mutant (V288I+L376P+E488V) is as high as 85% or more and even in the presence of sodium chloride, ATP could be detected with almost the same sensitivity as in the absence of sodium chloride even in the presence of sodium chloride.

Example 2

For the mutant beetle luciferase according to the present invention, the effect of sodium chloride concentration on luciferase activity was investigated. The wild-type *Photinus pyralis* luciferase, the mutant (V288I+L376P) and the mutant (V288I+E488V) prepared in Example 1 were used as the beetle luciferase.

Specifically, a reaction solution prepared by mixing 50 µL of the reaction buffer containing a beetle luciferase (0.5 mg/mL), 50 µL of D-firefly luciferin (produced by Wako Pure Chemical Industries, Ltd. 1.5 mM), 50 µL of an ATP solution (50 mM Tris-HCl buffer (pH 7.4) containing $2\times10^{-9}$M ATP, and 10 mM $MgCl_2$), and 50 µL of an aqueous sodium chloride solution (40 mM-2.4 M) or 50 µL of water was injected into each well of a 96-well plate (produced by Nunc, LumiNunc plate), respectively. Thereafter, the luminescence intensity was measured in a manner similar to Example 1. The final sodium chloride concentration of each reaction solution was 0, 10, 50, 100, 140, 200, 400, or 600 mM.

FIG. 1 is a plot diagram of luminescence intensity of each beetle luciferase for each sodium chloride concentration in the reaction solution. In addition, the sodium chloride concentration 140 mM corresponds approximately to the salt concentration of physiological saline. As a result, in the presence of 10 to 600 mM sodium chloride, both the mutant (V288I+L376P) and the mutant (V288I+E488V) had higher luminescence intensity than the wild-type and improved salt tolerance.

Example 3

The endotoxin was detected by using the mutant beetle luciferase according to the present invention. The wild-type *Photinus pyralis* luciferase and the mutant (V288I+E488V) prepared in Example 1 were used as the beetle luciferase.

Specifically, 100 µL of a test solution prepared by dissolving endotoxin in an ion exchanged water or 1.8% by mass aqueous sodium chloride solution was added to a lyophilized limulus reagent (produced by Wako Pure Chemical Industries, Ltd., Single Test Wako) and heated at 37° C. for 10 minutes. Subsequently, 50 µL of 75 µM luminescent substrate Bz-Leu-Gly-Arg-aminoluciferin aqueous solution was added and further heated at 37° C. for 5 minutes. After addition of 100 µL of this reaction solution to a 96-well plate (LumiNunc plate produced by Nunc), 50 µL of a reaction buffer (50 mM Tris-HCl buffer (pH 7.4) containing $2\times10^{-4}$M ATP, and 10 mM $MgCl_2$) containing a beetle luciferase (20 µg/mL) was added using an injector provided with a microplate reader (ARVO MX produced by Perkin-Elmer). Thereafter, the luminescence intensity of each reaction solution was measured in a manner similar to Example 1. The final endotoxin concentration of each reaction solution was 0, 0.001, or 0.005 EU/mL. Further, the final concentration of sodium chloride in the endotoxin solution containing sodium chloride was 0.9% by mass.

Figure 2:
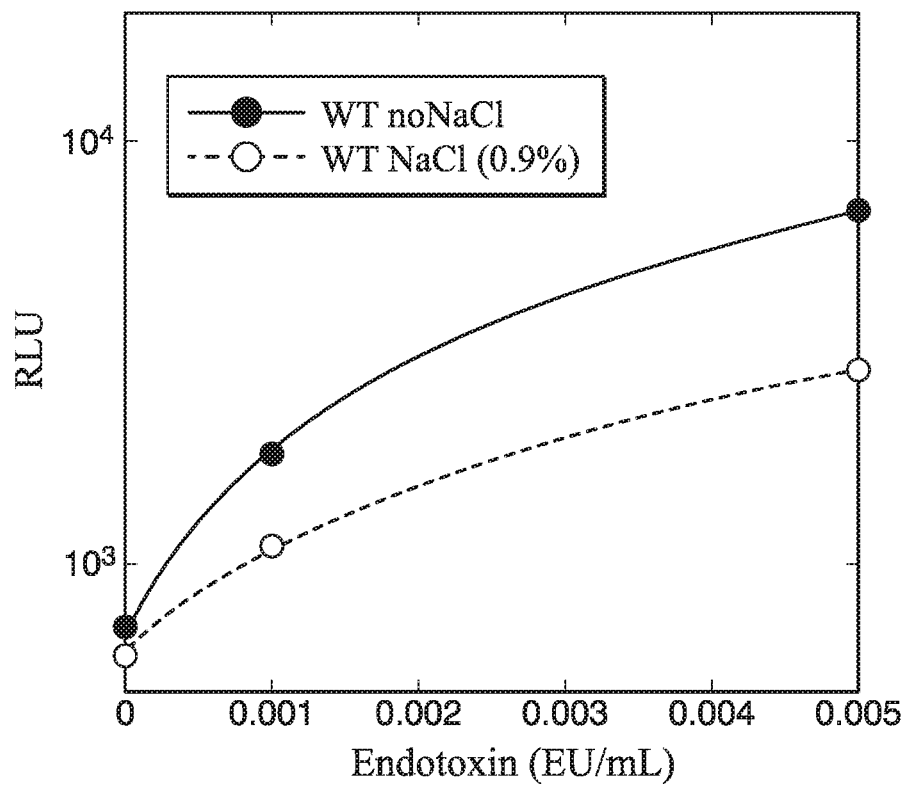
FIG. 2 is a plot diagram of measurement values of luminescence intensity (RLU) of wild-type *Photinus pyralis* luciferase for each endotoxin concentration (mM) in the reaction solution in Example 3.
Figure 3:
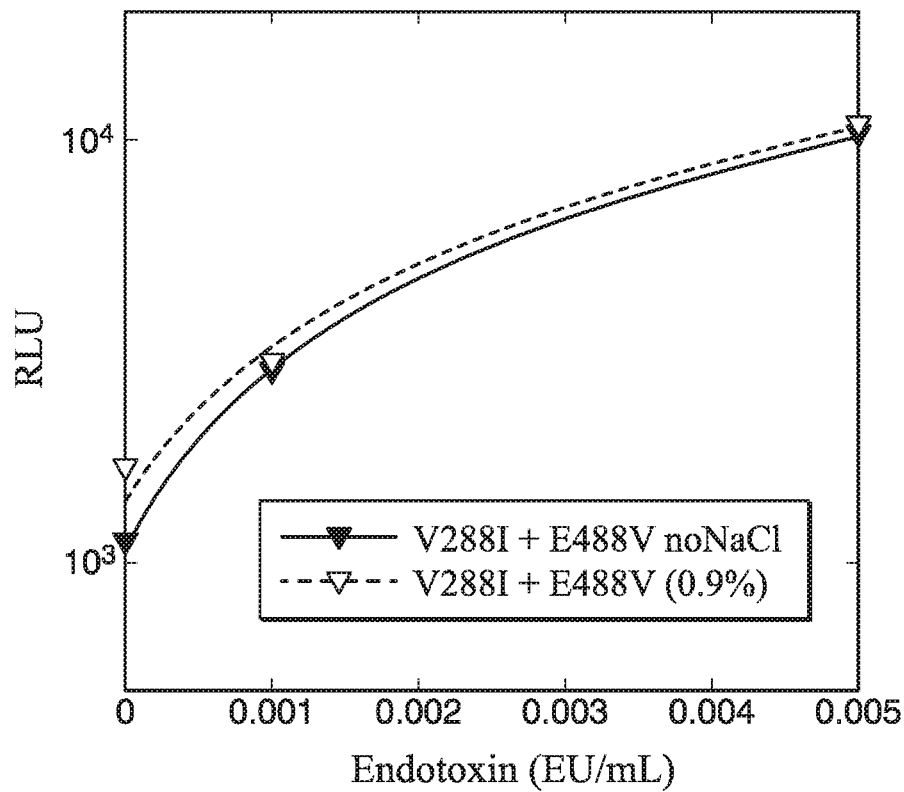
FIG. 3 is a plot diagram of measurement values of luminescence intensity (RLU) of mutant *Photinus pyralis* luciferase (the mutant (V288I+E488V)) for each endotoxin concentration (mM) in the reaction solution in Example 3.

FIGS. 2 and 3 are plot diagrams of measurement values of luminescence intensity of each beetle luciferase for each endotoxin concentration (EU/mL) in the reaction solution. FIG. 2 shows the result of wild-type *Photinus pyralis* luciferase, and FIG. 3 shows the results of the mutant (V288I+E488V). Further, in these figures, "no NaCl" is the result of the reaction solution containing no sodium chloride and "NaCl (0.9%)" is the result of the reaction solution containing sodium chloride. As a result, in the wild-type, the luminescence intensity in the reaction solution having a final concentration of 0.9% by mass sodium chloride was clearly weaker than the luminescence intensity in the reaction solution containing no sodium chloride and was detected less than the actual amount of endotoxin. On the contrary, in the mutant (V288I+E488V), the luminescence intensity in the reaction solution of 0.9% by mass sodium chloride was almost the same as the luminescence intensity in the reaction solution containing no sodium chloride, and was confirmed that it was not susceptible to luminescence inhibition by sodium chloride.

Sequence Listing Free Text

---

What is claimed is:

1. A mutant *Photinus pyralis* luciferase having mutations in an amino acid sequence of a wild-type *Photinus pyralis* luciferase, said mutations consisting of:
  (a) a mutation in which the amino acid corresponding to valine at position 288 in the amino acid sequence of the wild-type *Photinus pyralis* luciferase is isoleucine, leucine, or phenylalanine; and
  (b) a mutation in which the amino acid corresponding to glutamic acid at position 488 in the amino acid sequence of the wild-type *Photinus pyralis* luciferase is valine, alanine, serine, leucine, isoleucine or phenylalanine; and
  wherein a luminescence intensity of the mutant *Photinus pyralis* luciferase due to a luciferin-luciferase luminescence reaction in a 0.9% by mass sodium chloride solution is 50% or more with respect to that in a sodium chloride-free solution, and
  the luminescence intensity of the mutant *Photinus pyralis* luciferase due to the luciferin-luciferase luminescence reaction in the 0.9% by mass sodium chloride solution is greater than that of the wild-type *Photinus pyralis* luciferase.

2. The mutant *Photinus pyralis* luciferase according to claim 1, wherein the mutations of (a) and (b) are the following mutations (a') and (b'), respectively:
  (a') a mutation in which the amino acid corresponding to valine at position 288 in the amino acid sequence of the wild-type *Photinus pyralis* luciferase is isoleucine; and
  (b') a mutation in which the amino acid corresponding to glutamic acid at position 488 in the amino acid sequence of the wild-type *Photinus pyralis* luciferase is valine.

3. A gene encoding the mutant *Photinus pyralis* luciferase according to claim 1.

4. A recombinant vector containing the gene according to claim 3.

5. A transformant having the recombinant vector according to claim 4.

6. A method for preparing a mutant *Photinus pyralis* luciferase, comprising steps of culturing the transformant according to claim 5 to obtain a culture and collecting the mutant *Photinus pyralis* luciferase from the culture obtained in the culturing step.

* * * * *